United States Patent [19]

Lindsey et al.

[11] Patent Number: 5,118,452

[45] Date of Patent: Jun. 2, 1992

[54] METHOD OF ATTACHING A HAPTIC TO AN OPTIC OF AN INTRAOCULAR LENS

[75] Inventors: Raymie H. Lindsey; Anilbhai S. Patel, both of Arlington, Tex.; John G. Marshall, III, Bellevue, Wash.; John M. Smith, Garberville, Calif.

[73] Assignee: Nestle S.A., Vevey, Switzerland

[21] Appl. No.: 682,113

[22] Filed: Apr. 5, 1991

[51] Int. Cl.⁵ .............................. B29D 11/00
[52] U.S. Cl. ..................... 264/1.4; 156/272.8; 264/1.7
[58] Field of Search ................ 264/1.4, 1.7; 256/272.8

[56] References Cited

U.S. PATENT DOCUMENTS

| | | | |
|---|---|---|---|
| 3,994,027 | 11/1976 | Jensen et al. | 3/13 |
| 4,104,339 | 8/1978 | Fetz et al. | 264/249 |
| 4,150,471 | 4/1979 | Richards et al. | 264/249 |
| 4,307,043 | 12/1981 | Chase et al. | 264/1.7 |
| 4,668,446 | 5/1987 | Kaplan et al. | 264/1.7 |
| 4,786,445 | 11/1988 | Portnoy et al. | 264/1.7 |
| 4,834,749 | 5/1989 | Orlosky | 264/1.7 |
| 4,834,751 | 5/1989 | Knight et al. | 264/1.7 |
| 4,843,209 | 6/1989 | Mulligan | 219/121.63 |
| 4,863,539 | 9/1989 | Lee et al. | 264/1.7 |
| 4,894,062 | 1/1990 | Knight et al. | 623/6 |

Primary Examiner—James Lowe
Attorney, Agent, or Firm—Julie J. Cheng; Jeffrey S. Schira

[57] ABSTRACT

A method for attaching a polymethylmethacrylate haptic having a colored core to an optic of an intraocular lens, containing the steps of providing the periphery of the optic with a pair of intersecting holes, inserting an end of the haptic into one hole, inserting an end of a polymethylmethacrylate anchor strand having a colored core into the second hole so that the end of the anchor strand and the end of the haptic intersect, aiming a laser capable of a transmitting energy of a visible wavelength at the intersection of the first and second holes, firing the laser through the optic at the point of intersection of the end of the haptic and the end of the anchor strand, wherein the optic transmits, but essentially does not absorb, the laser energy and the core the anchor strand and the core of the haptic absorb a portion of the laser energy sufficient to fuse the end of the anchor strand and the end of the haptic at their point of intersection.

16 Claims, 4 Drawing Sheets

METHOD OF ATTACHING A HAPTIC TO AN OPTIC OF AN INTRAOCULAR LENS

BACKGROUND OF THE INVENTION

The present invention relates to intraocular lenses, particularly to methods for attaching a haptic to an optic using laser welding.

Intraocular lenses have been known since about 1950. They are used to replace the natural lenses of eyes which have been damaged by trauma or disease, such as cataracts. A typical intraocular lens (IOL) comprises an artificial lens ("optic") and at least one support member ("haptic") for positioning the IOL in the eye. The optic may be formed from any of a number of different materials, including polymethylmethacrylate (PMMA), and it may be hard, relatively flexible or even fully deformable in order to permit the IOL to be rolled or folded and inserted through a relatively small incision in the eye. The haptic is generally made of some resilient material, such as polypropylene or PMMA. IOL's may be characterized as either "one-piece" or "multi-piece." In the one-piece IOL's, the haptic and the optic are integrally formed and the IOL is then cut to the desired shape and configuration. The multi-piece IOL's are formed either by attaching the haptic to a pre-formed optic or by molding the optic around an end portion of the haptic.

U.S. Pat. Nos. 4,834,751 and 4,894,062 (both Knight, et al.) describe haptic attachment methods whereby a haptic and an anchoring member are joined, then an optic is molded around the end portion of the haptic having the anchoring member joined. While these methods provide strong haptic-optic interlock, the procedure for molding an optic around previously joined haptic and anchor members is complex and requires special care to maintain the haptic in place while the optic material is being cured and to remove the mold without damaging the haptic.

Many methods for attaching a haptic to a pre-formed optic are known, including those involving the use of adhesives. If an adhesive is used to attach a haptic to an optic, the adhesive must be strong, biologically inert and resistant to degradation by bodily fluids. At present, there are few materials which would satisfy all these requirements. In addition, there is a danger that the adhesive would deteriorate over time, resulting in loose or detached haptics within the eye.

Other, more common, methods for attaching a haptic to a pre-formed optic involve the use of heat. One such haptic attachment method involves drilling intersecting holes into the periphery of an optic and inserting one end of the haptic into one of the holes. A heated probe is then inserted through the other hole, contacting the haptic and causing a portion of it to melt into the second hole. When the haptic end portion hardens, a mechanical interlock with the optic is formed. A similar method is disclosed in U.S. Pat. No. 4,104,339 (Fetz, et al.), where a haptic hole is made in the peripheral edge of an optic, the haptic end is inserted into the hole and then an inductively heated thin probe is pushed through the posterior face of the optic into contact with the haptic end to form a fused connection between the haptic and the optic. This is currently the most common method for attaching a haptic to an optic.

Another such method is disclosed in U.S. Pat. No. 4,307,043 (Chase, et al.), where a hole having threaded recesses is made through a portion of the optic (the hole being essentially parallel to the plane of the optic) and one end of a haptic is inserted through the hole so that it projects beyond the optic. Heat is then applied to the haptic end projecting beyond the optic to melt a portion of it, which fills the threaded portions of the hole. When the haptic material hardens, a mechanical interlock with the optic is formed.

These heat attachment techniques described above are disadvantageous in that skilled technicians are required and/or there is danger of damage to the optic.

U.S. Pat. No. 4,786,445 (Portnoy, et al.) discloses another haptic attachment method which involves making a cavity in the periphery of an optic, wherein the innermost portion of the cavity has a shoulder. A haptic end portion is inserted into the cavity and laser energy of a near infrared wavelength is transmitted through the optic to the haptic, causing it to melt and flow into the shoulder of the cavity. When the end portion hardens, a mechanical interlock between the haptic and the optic is formed. Although this method avoids some of the problems of the prior-mentioned methods, there are other disadvantages. Because the haptic end is melted to form a shoulder within the cavity of the optic, there is a likelihood of variation in haptic length, both between individual IOL's and between individual haptics attached to the same IOL.

SUMMARY OF THE INVENTION

This invention is directed to methods for attaching a haptic to an optic without damaging the optic while producing a strong mechanical interlock between the haptic and the optic. This is accomplished by forming two separate, intersecting holes within the periphery of an optic, inserting the end portion of a haptic into one hole, inserting an anchor strand into the second hole so that the two strands intersect and transmitting laser energy of a visible wavelength through the optic to the intersection of the two strands, whereby the anchor strand and the haptic end portion are fused, forming a solid junction and mechanically anchoring the haptic within the optic. Use of a laser transmitting energy in the visible region of the spectrum is less hazardous than use of other forms of laser energy since the laser beam is easily seen and thus more readily avoided.

DETAILED DESCRIPTION OF THE INVENTION

Figures 1, 2:
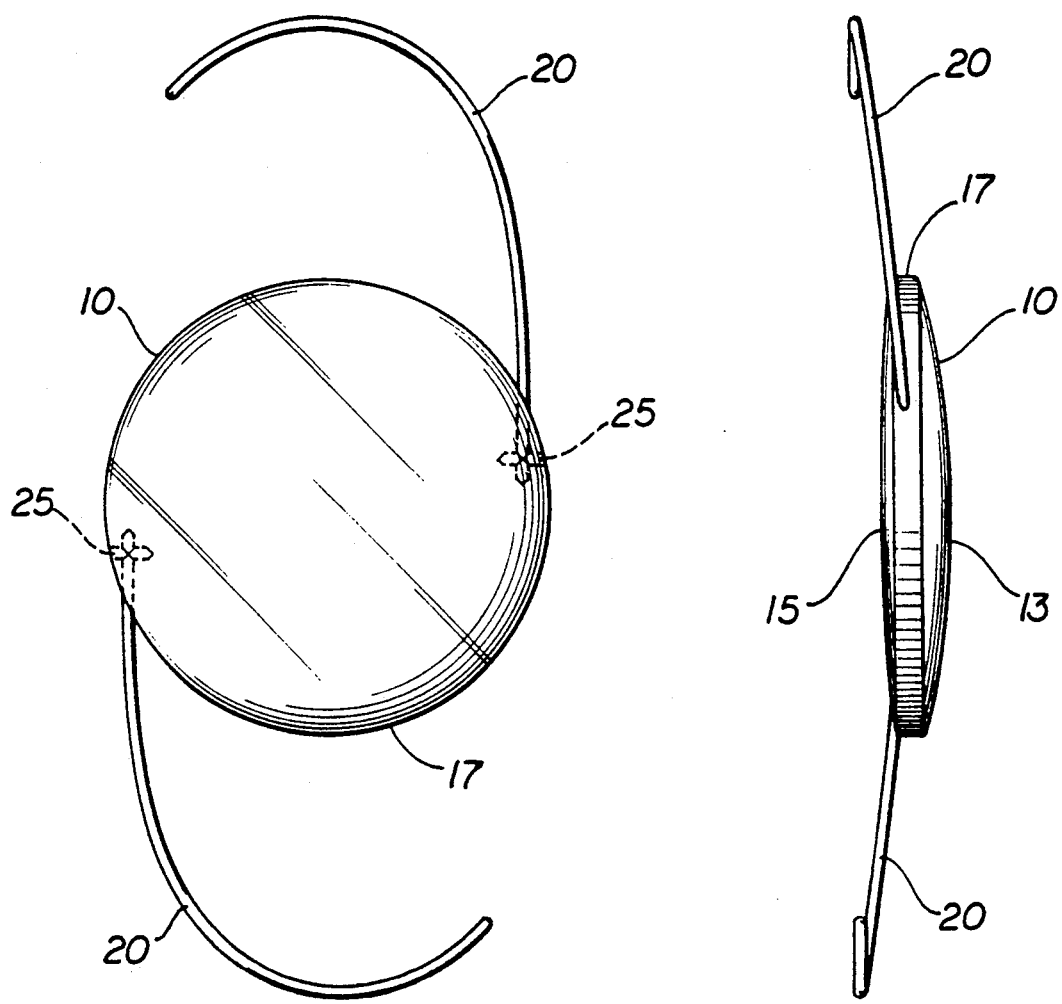
FIG. 1 is an elevational view of a typical IOL made in accordance with the methods of the present invention.
FIG. 2 is a side elevation view of a typical IOL, such as shown in FIG. 1, made in accordance with the methods of the present invention.
Figures 3, 4:
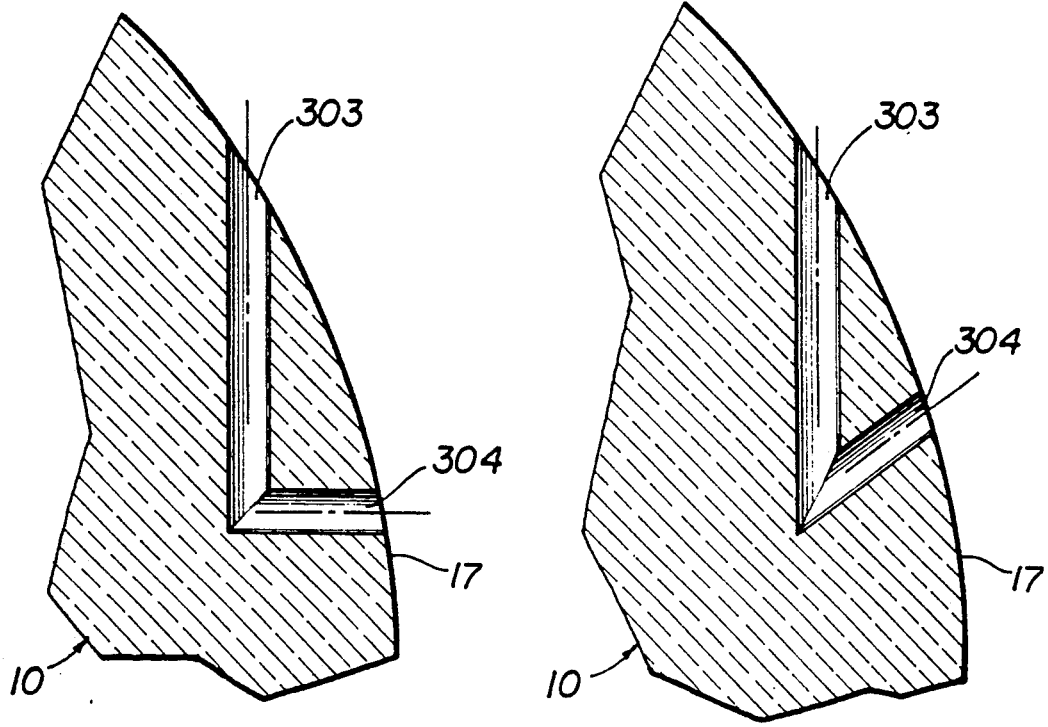
FIGS. 3, 4, and 5 are fragmentary sectional views of optics, showing alternative hole configurations for attaching haptics in accordance with the methods of the present invention.
Figure 5:
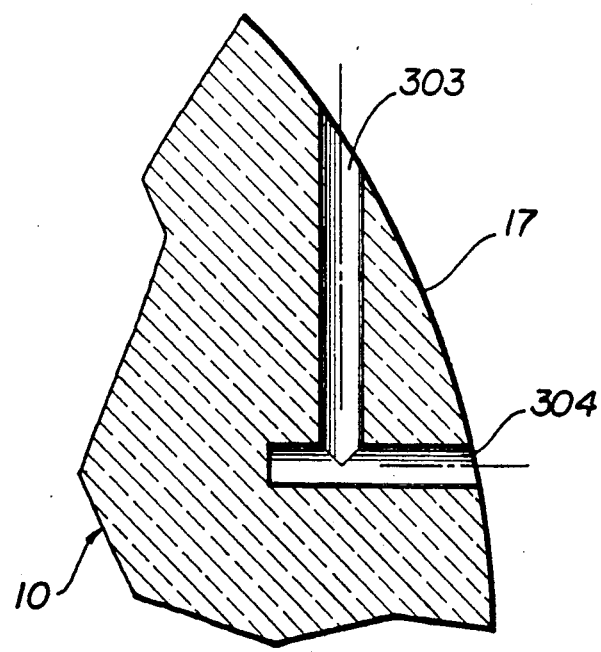

A typical IOL, shown in FIGS. 1 and 2, includes an optic 10 and two identical haptics 20. The haptics 20 may be configured in any of a number of ways and the optic 10 may have any of a number of shapes. The optic shape and haptic configuration shown in FIGS. 1 and 2 are illustrative only and are not meant to be limiting.

As shown in FIG. 2, the optic 10 has an anterior face 13, a posterior face 15 and a peripheral edge 17. The optic may be made of any of a number of known materials, including, but not limited to: PMMA and soft acrylics, silicones, or hydrogels. Preferred optic materials are the high refractive index copolymers disclosed in copending, commonly assigned, U.S. patent application Ser. No. 07/609,863 filed on Nov. 7, 1990.

The haptics 20 are formed separately from the optic 10 and then attached along a portion of the peripheral edge 17. At least the haptic end portion to be attached to the optic must comprise non-transparent or colored material which is capable of absorbing visible wavelength laser energy. The haptics may be made of any of a number of resilient polymeric materials including, but not limited to: PMMA, polypropylene, polyimides and polyvinylidene difluoride. The haptic material may either be different from or the same as the optic material. Haptic material which is transparent and non-colored must either include a dye or be combined with a colored material, such as by using a colored core. The preferred haptic materials are PMMA with a copper phthalocyanine-doped core and blue propylene.

The anchor strand which is joined to the haptic end portion in the optic must also comprise a non-transparent or colored material capable of absorbing visible wavelength laser energy and may be made of any haptic material. The anchor strand and haptic end portion must be made of materials capable of fusing to one another, preferably the same material. The anchor strand may be either: a short strand of haptic material which, when attached, will fit completely within the second hole of the optic; a long strand of haptic material which is severed at the optic periphery after the haptic end portion has been joined to it; or the other end portion of the haptic.

Figure 9:
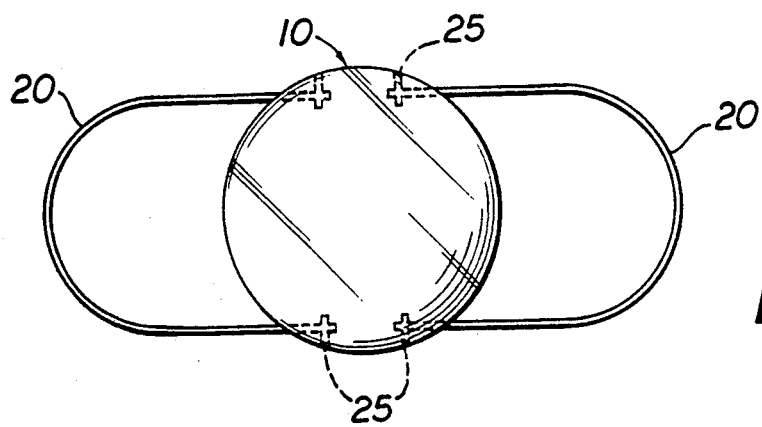
FIGS. 9, 10, and 11 are elevational views of IOL's, showing alternative haptic configurations, wherein the haptics are attached in accordance with the methods of the present invention.
Figure 10:
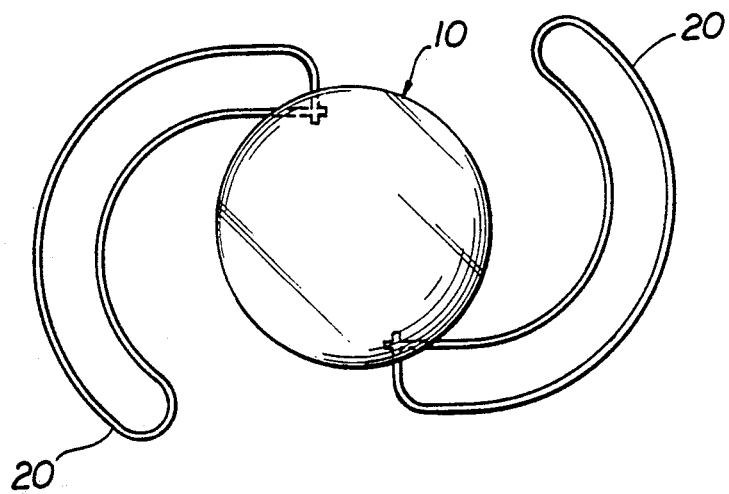
Figure 11:
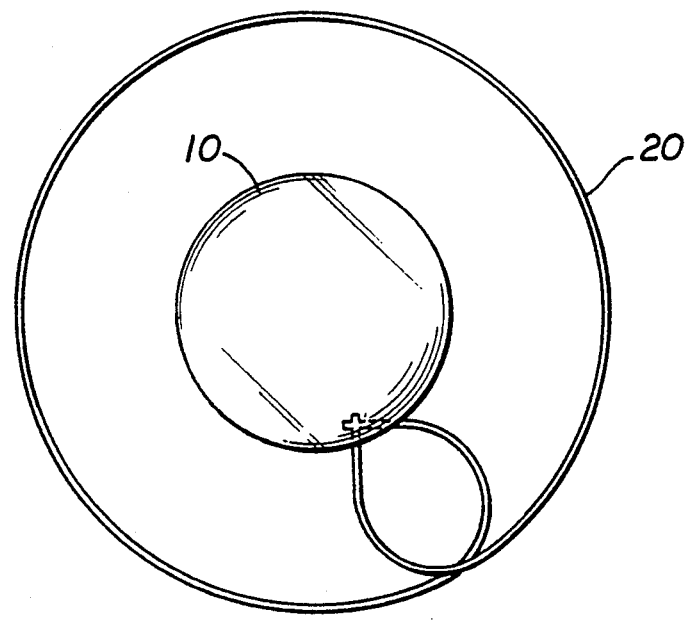

If loop haptic configurations are desired, each end of a haptic will be attached to the optic. For example, FIG. 9 illustrates a loop configuration wherein each end of a haptic is attached by a set of intersecting holes. FIGS. 10 and 11 illustrate alternative loop configurations where the second end of the haptic is the anchor strand.

The laser used to weld the haptic to the optic is one capable of transmitting energy in the visible region of the spectrum, approximately 450 to 750 nanometers (nm). Visible wavelength laser energy will be at least partially absorbed by the non-transparent or colored haptic material, regardless of the specific wavelength of energy used; however, it is preferable that the laser energy used is coordinated with the color of the haptic to be attached. For example, if a blue haptic is to be attached, laser energy having a wavelength in the blue portion of the visible spectrum is preferred. An Argon laser capable of transmitting energy between about 450 and about 550 nm is preferred.

The intersecting holes in the optic may be made in any suitable manner and be made either after the optic has been formed or the optic may be formed with preformed holes. As shown in FIGS. 3, 4, 5 and 8, the holes may end at the point of intersection (the embodiments shown in FIGS. 3 and 4), or one or both holes may extend beyond the intersection (the embodiments shown in FIGS. 5 and 8). It is preferred that the intersecting holes are perpendicular to one another and that at least one hole extends beyond the intersection. It is most preferred that the intersecting holes are perpendicular to one another and that both holes extend beyond the intersection.

To attach a haptic to an optic having intersecting holes, one end of a haptic is inserted fully into the first hole and one end of an anchor strand is inserted into the second hole so that the anchor strand and haptic intersect. A laser capable of generating energy of a visible wavelength is then aimed at the intersection of the first and second holes and the laser is fired to fuse the anchor strand and the haptic at their point of intersection.

The following is an example of a method of the present invention, wherein the optic is made of a soft material, such as the high refractive index copolymers disclosed in U.S. patent application Ser. No. 07/609,863. Reference numerals refer to FIGS. 1, 2 and 6 through 8.

EXAMPLE

Figure 6:
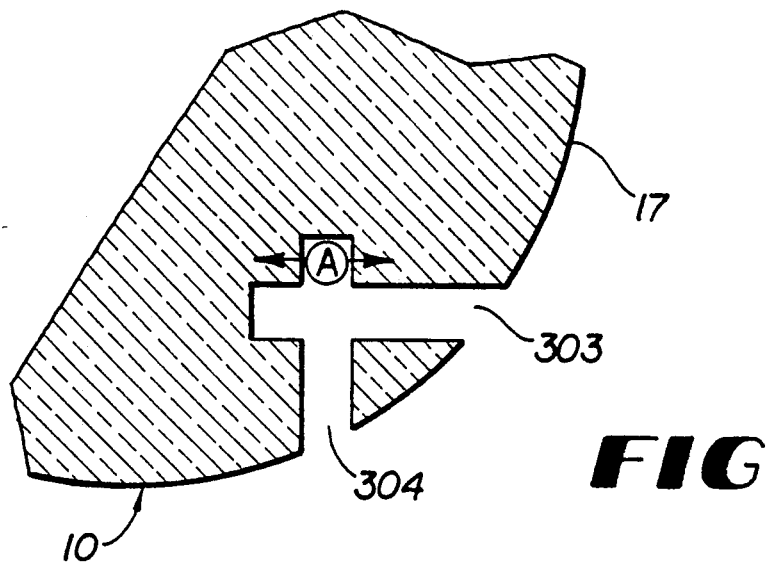
FIGS. 6, 7, and 8 are fragmentary sectional views of a typical optic, showing holes for attaching haptics.
Figure 7:
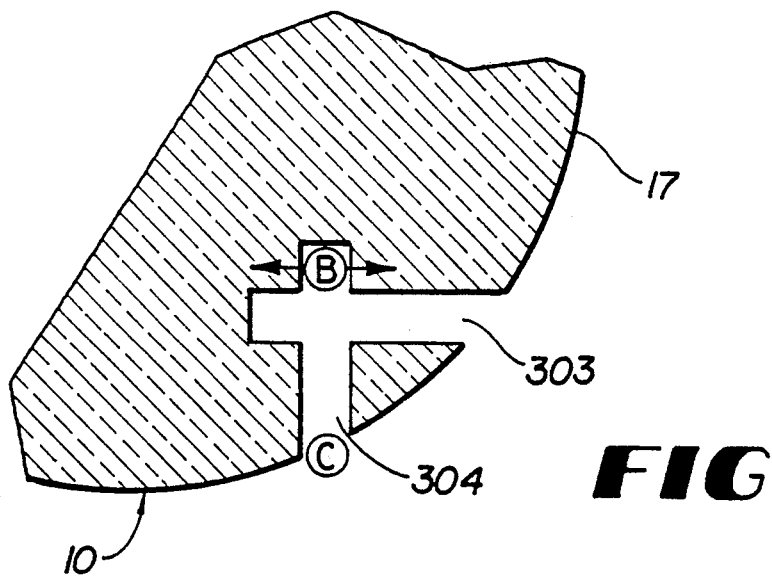
Figure 8:
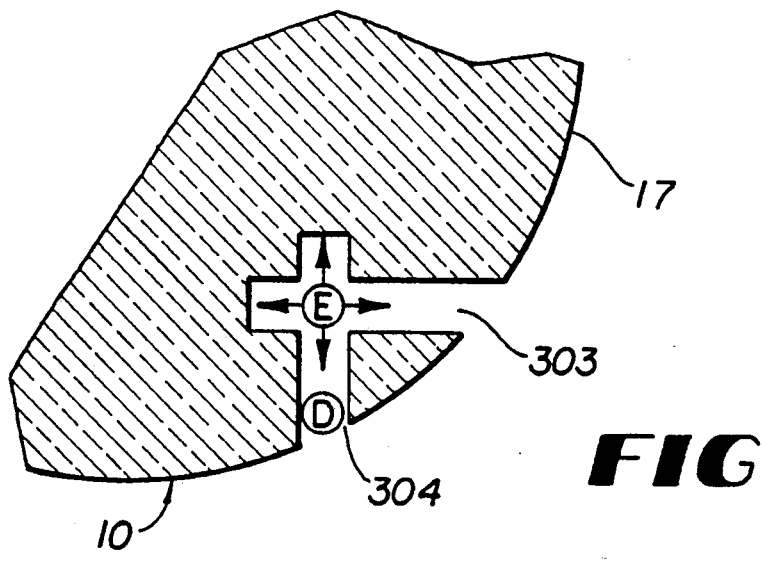

The haptic 20 is inserted fully into hole 303 and is inserted into hole 304 to the point where the optic 10 distorts, as shown in FIG. 6. A laser is then aimed and fired at point A. While firing, the laser is moved back and forth in the direction of the arrows shown in FIG. 6 until the optic relaxes, as shown in FIG. 7. The process of feeding the haptic anchor 25 into the anchor hole 304 and then firing the laser at point A is repeated as many times as necessary until the back of anchor hole 304 is full of material. The laser is then aimed at point C (FIG. 7) and fired until the haptic anchor strand 25 is severed. The laser is then aimed at point B (FIG. 8) and fired, causing the severed end of the haptic anchor strand 25 to draw into the hole 304. The laser is then aimed at point E (FIG. 8) and fired, moving in all directions shown by the arrows in FIG. 8 until the weld is smooth. Additional haptics 20 are attached to the optic 10 in the same manner.

After the optic has been cured but before the optic is removed from the mold, the molded optic is cooled to less than 10° C. and preferably less than 0° C. Two substantially perpendicular holes are drilled into a portion of the peripheral edge so that each hole extends slightly beyond the point of intersection. The drilling operation is repeated for each additional haptic end to be attached. After all of the drilling has been completed, the optic is removed from the mold.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for attaching a haptic to an optic of an intraocular lens, comprising the steps of:
    providing the periphery of the optic with a first and a second hole, said holes intersecting;
    fully inserting an end of the haptic into said first hole, said haptic being made from clear polymethylmethacrylate surrounding a colored polymethylmethacrylate core;
    inserting an end of an anchor strand into said second hole, said end of the anchor strand and said end of the haptic intersecting and said anchor strand being made from clear polymethylmethacrylate with a colored polymethylmethacrylate core;

aiming a laser capable of a transmitting energy of a visible wavelength at the intersection of said first and second holes; and firing said laser through the optic at the intersection of said first and second holes, wherein the optic transmits, but essentially does not absorb, the laser energy and the colored core of the anchor strand and the colored core of the haptic absorb a portion of the laser energy sufficient to fuse said end of the anchor strand and said end of the haptic at their point of intersection.

2. The method of claim 1 wherein the core of the colored haptic comprises copper phthalocyanine-doped polymethylmethacrylate.

3. The method of claim 2 wherein the core of the colored anchor strand comprises copper phthalocyanine-doped polymethylmethacrylate.

4. The method of claim 1 wherein said laser energy has a wavelength from about 450 nm to about 550 nm.

5. The method of claim 4 wherein said laser energy is provided by an Argon laser.

6. The method of claim 5 wherein said laser energy has a wavelength of about 488 nm.

7. The method of claim 1 wherein said first and second holes are perpendicular.

8. The method of claim 7 wherein said first and second holes are planar to the optic.

9. The method of claim 1 wherein said end of an anchor strand is inserted into said second hole prior to inserting said end of the haptic.

10. The method of claim 1 wherein said first and second holes are drilled into the periphery of the optic, which has been cooled.

11. The method of claim 10 further comprising the steps of inserting said end of an anchor strand further into said second hole and repeating the previous steps of aiming and firing said laser.

12. The method of claim 10 further comprising the steps of:

severing said end of an anchor strand at a point beyond the periphery of the optic; and aiming and firing said laser at a point within said second hole just inside the periphery of the optic, said laser energy being sufficient to melt or soften the severed end of the anchor strand to fill a portion of said second hole.

13. The method of claim 1 wherein said end of an anchor strand is the second end of the haptic.

14. A method for attaching a haptic to a soft optic of an intraocular lens, comprising the steps of:

cooling the optic to a temperature below about 10° C.;

providing the peripheral edge of the optic with a first and a second hole, said holes intersecting;

fully inserting an end of the haptic into said first hole, said end of the haptic comprising a material capable of absorbing visible wavelength laser energy;

inserting an end of an anchor strand comprising haptic material into said second hole, said end of an anchor strand and said end of the haptic intersecting;

aiming a laser capable of transmitting energy of a visible wavelength at the intersection of said first and second holes; and firing said laser through the optic at the intersection of said first and second holes, wherein the optic transmits, but essentially does not absorb, the laser energy and said end of an anchor strand and said end of the haptic absorb a portion of the laser energy sufficient to fuse said end of an anchor strand and said end of the haptic at their point of intersection.

inserting said anchor strand further into said second hole and repeating the previous steps of aiming and firing said laser;

severing said anchor strand at a point beyond the peripheral edge of the optic; and aiming and firing said laser at a point within said second hole just inside the peripheral edge of the optic, said laser energy being sufficient to melt the severed end of said anchor strand to fill a portion of said second hole.

15. The method of claim 14 wherein each of said end of the haptic and said end of an anchor strand comprises blue-colored material.

16. The method of claim 15 wherein each of said end of the haptic and said end of an anchor strand comprises polymethylmethacrylate with a copper phthalocyanine-doped core.

* * * * *